United States Patent [19]

Kornbaum et al.

[11] Patent Number: 4,616,046

[45] Date of Patent: Oct. 7, 1986

[54] STERILIZATION OF OBJECTS MADE OF HALOGENO-VINYLIC POLYMERS USING IONIZING RADIATION

[75] Inventors: Simon Kornbaum, Caluire; Jean-Yves Chenard, Pau, both of France

[73] Assignee: Ato Chimie, France

[21] Appl. No.: 607,510

[22] Filed: May 7, 1984

Related U.S. Application Data

[63] Continuation-in-part of Ser. No. 565,522, Dec. 27, 1983, abandoned, which is a continuation of Ser. No. 309,434, Oct. 7, 1981, abandoned.

[30] Foreign Application Priority Data

Oct. 10, 1980 [FR] France ................... 80 21662

[51] Int. Cl.[4] .................. C08K 5/57; C08K 5/58; C08J 3/28
[52] U.S. Cl. ...................... 522/79; 524/180; 524/181; 524/183; 524/302
[58] Field of Search ............... 524/180, 181, 183, 302; 204/159.2; 252/399; 522/79

[56] References Cited

U.S. PATENT DOCUMENTS

| | | |
|---|---|---|
| 3,167,527 | 1/1965 | Hechenbleikner et al. ........ 524/180 |
| 3,928,285 | 12/1975 | Gough et al. ...................... 524/180 |
| 4,036,719 | 7/1977 | Lyons ............................... 204/159.2 |
| 4,086,411 | 4/1978 | Nagano et al. .................. 204/159.2 |
| 4,180,447 | 12/1979 | Sencar ............................. 204/159.2 |
| 4,336,168 | 6/1982 | Hoch et al. ......................... 524/302 |
| 4,412,897 | 11/1983 | Kornbaum et al. ................. 524/180 |

FOREIGN PATENT DOCUMENTS 2434835  3/1980  France .

OTHER PUBLICATIONS

W. Szymanski et al.: J. Applied Polymer Science, vol. 23, 791-795 (1979).
S. V. Krylova et al.: Plast. Massey, vol. 15, 16-17 (1973).
G. Lerke et al.: J. Applied Polymer Science, vol. 28, 501-511 (1983).
G. Lerke et al.: J. Applied Polymer Science, vol. 28, 519-529 (1983).
I. Lerke et al.: J. Applied Polymer Science, vol. 28, 513-518 (1983).
Kim et al.: Chongi Hakhoe Chi., vol. 26, 185-190 (1977).

*Primary Examiner*—Veronica P. Hoke
*Attorney, Agent, or Firm*—Ostrolenk, Faber, Gerb & Soffen

[57] ABSTRACT

A process for the sterilization of objects made of polymers in which the molecule contains a halogen, or of products packaged in such polymer material, the polymer containing a heat stabilizer wherein, prior to irradiation of the object or the package and its contents, there is incorporated into the polymer one or more esters carrying at least one mercaptan function in the proportion of one —SH group for 3 to 10 carbon atoms.

30 Claims, No Drawings

STERILIZATION OF OBJECTS MADE OF HALOGENO-VINYLIC POLYMERS USING IONIZING RADIATION

This is a continuation-in-part of application Ser. No. 565,521, filed Dec. 27, 1983 now abandoned which was a continuation of application Ser. No. 309,434, filed Oct. 7, 1981, now abandoned.

This invention relates to an improved process of sterilization using ionizing radiation applied to objects of plastics material based on polymers whose molecules contain a halogen. The invention is particularly appropriate to articles made of halogenovinyl polymers or vinylidene polymers, and especially to those of polyvinyl chloride and to copolymers of polyvinyl chloride.

Sterilization by irradiation using ionizing rays, that is to say high-energy radiation, notably X-rays, gamma rays, beta rays, etc. is known: it has been described for example in the proceedings of the conference in Deauville on Nov. 10, 1977 organized by SNPM Bio-Conseil Neuilly (in an articale by Icre and Vidal). The process is very beneficial when one wishes to ensure the proper preservation of a product or food commodity in a container. If the product is not adversely affected by a brief irradiation, one subjects the closed container which contains the product to ionizing rays which are capable of traversing the walls of the container. This results in a rapid sterilization, to the heart of the contents. As a consequence, no further contamination can then occur if the walls of the container are impermeable to microorganisms, which is the case with walls made of halogenovinylic polymers and the like. However, it is necessary that the material of which the container is made should remain unaltered by this treatment; beyond a certain radiation dose, necessary for the sterilization, the ionizing radiation produces alterations in the mass of many resins, in particular in those of polyvinyl chloride and its copolymers, the effect manifesting itself as a coloration of the material, which may be more or less intense depending upon various factors.

Thus, for example, in the case of molded objects, of polyvinyl chloride heat stabilized by conventional adjuvants, notably organo-stannic compounds and thio compounds, yellowing occurs as soon as the dose of gamma rays reaches about 0.5 megarad. The change becomes extremely marked when the dose is of the order of 1 megarad, and it reaches a highly unacceptable level at 2.76 megarads, bearing in mind that the sterilization can require doses of 1 to 2.76 megarads or more.

It is not surprising that the conventional heat stabilizers for halogeno-resins, in particular the organo-stannic compounds accompanied by organic thio compounds, do not protect these resins against the adverse effects of ionizing radiation, because this latter action is of a different nature as compared with that of heating. What is astonishing however is that the presence of certain specific mercaptans, in conjunction with other standard stabilizers, enables one to prevent the alteration of the resins in question for doses of ionizing radiation up to about 2.8 megarads or more. It is upon this unexpected discovery that the present invention is based.

The invention offers the important advantage of permitting stabilization with respect to ionizing radiation of polymers containing plasticizers and those which are free from plasticizers. It has been considered up till now that only certain plasticizers would enable the appearance of polyvinyl chloride to be improved in relation to gamma rays. Thus, it has been stated, in Chemical Abstracts Vol. 61 (1964), 3263, in the publication of Tadashi Kimura (Osaka Munic. Tech. Res. Inst. Japan), that of those plasticizers of the phosphate type, bis(2-ethyl hexyl)sebacate or bis(2-ethyl hexyl)phthalate would give favorable results from this point of view. However, in practice, one is frequently looking to subject to ionizing radiation a resin which does not have to contain a plasticizer. One important case is that of the sterilization of products or foodstuffs contained in bottles or other packages of polyvinyl chloride. For one thing, good mechanical behavior of the package demands a sufficient rigidity, and thus absence of plasticizer; additionally there is a risk of the plasticizer contaminating the packaged product, which expresses itself in particular as a health hazard for food, cosmetic, hygienic or pharmaceutical products.

In accordance with the invention, an improved process for the sterilization of objects of plastics material in which the molecule contains a halogen, comprises incorporating into the plastics material, containing a standard stabilizer, preferably organo-tin and/or organo-antimony, one or more esters bearing the mercaptan function (—SH) in the proportion of one —SH group for 3 to 10 carbon atoms, and subjecting the object made out of the material so obtained to an ionizing radiation at a dosage of 0.5 to 2.8 or more megarads.

The polymer of the object thus sterilized remains colorless or slightly yellowish, if it was not colored to start with. This means as a result that the objects obtained by the application of the process of the present invention are characterized by the similarity of their color to that of the polymer which is used.

The resins to which the novel process is applicable are constituted generally by the various polymers in which the molecule includes halogen atoms. These are, more especially, halogenovinylic resins, the more important industrial types of which are chlorinated polyethylene, vinylidene polydichloride, polyvinyl acetochloride, chloropolyether, polychlorotrifluoroethylene, polyfluorovinylidene, polyvinyl fluoride, the various corresponding copolymers, notably those of vinyl chloride with vinyl acetate, vinyl chloride with that of vinylidene or with olefins, etc.

The standard heat stabilizers, the presence of which is necessary in the resins prior to their treatment in accordance with the invention, are known in the art. One can cite as prime examples the following compounds:

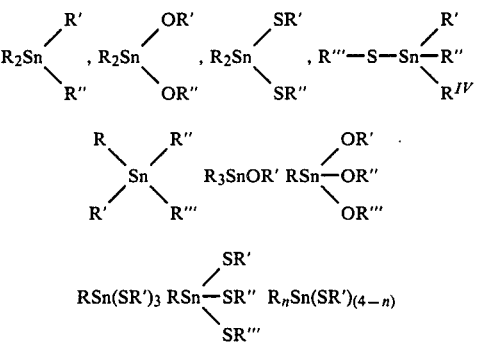

-continued

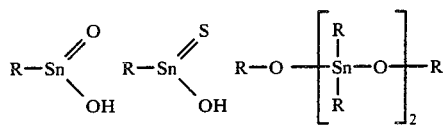

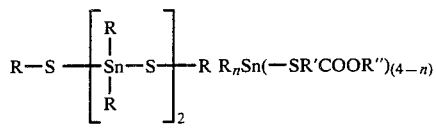

$R_nSn(-SR'OOCR'')_{(4-n)}$  $R_nSn(-OOCR')_{(4-n)}$

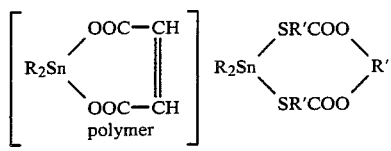

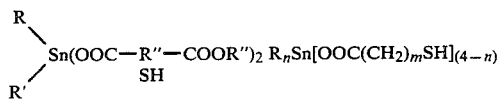

$\underset{R'}{\overset{R}{\diagdown}}Sn(OOC-R''-COOR'')_2$  $R_nSn[OOC(CH_2)_mSH]_{(4-n)}$

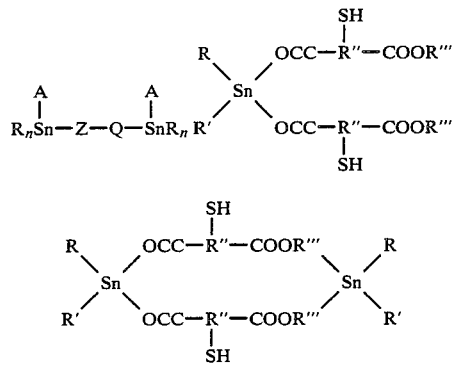

and similar substances in which the symbols R, R', R", R''', R$^{IV}$ designate different organic groups, and even inorganic groups, for example, hydrocarbyls and, more particularly, alkyl of 1–18 carbon atoms, preferably C$_{3-12}$ alkyl groups; R$^V$ is a C$_2$ to C$_6$ alkenyl; R$^{VI}$ is a trivalent hydrocarbyl group having 1 to 6 carbon atoms, Z is an organic divalent group having 2 to 8 carbon atoms; Q is S or $$\overset{O}{\underset{}{\overset{\parallel}{C}}}-O-;$$

A is a carboxyl containing moiety; n is 1, 2 or 3; and m is 1–7. The following compounds are notable examples:

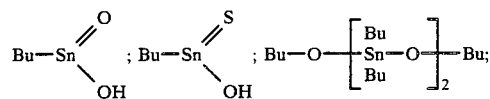

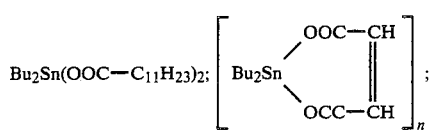

-continued

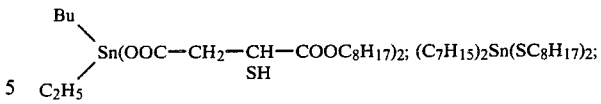

$Bu_2Sn(OCC-CH_2SH)_2;$ $(C_{10}H_{21})_2Sn(OCH_3)_2;\ (C_8H_{17})_2Sn(SCH_2-COOC_8H_{17})_2$ $Bu_2Sn(SC_8H_{17}COOC_{11}H_{23})_2\ BU_2Sn(SCH_2OOC-C_8H_{17})_2$

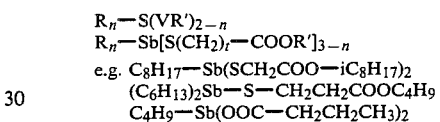

The stannic compounds can be replaced or accompanied by the equivalent combinations of antimony. Usable antimony derivatives include:

$R_n-S(VR')_{2-n}$
$R_n-Sb[S(CH_2)_t-COOR']_{3-n}$
e.g. $C_8H_{17}-Sb(SCH_2COO-iC_8H_{17})_2$
$(C_6H_{13})_2Sb-S-CH_2CH_2COOC_4H_9$
$C_4H_9-Sb(OOC-CH_2CH_2CH_3)_2$ where t is an integer of 1 to 7, n is 0–3 and R and R' are as defined above. Other metallic compounds could also be used. Such additional metallic heat stabilizers which can be employed include combinations of barium compounds and cadmium compounds, and also compounds of zinc, magnesium and calcium.

Typical examples including carboxylates and phenates of barium and cadmium, phthalates, sulfates, oxides, phosphates of lead, and the like.

One example, particularly useful, is mixtures of calcium and zinc salts of carboxylic acids which are added, as is known, to the resin jointly with an epoxidized oil. Thus, the tin or antimony heat stabilizer may be replaced, according to the invention, by a mixture of calcium carboxylate and zinc carboxylate, while an epoxidized oil, such as, for example, epoxidized soya bean or linseed oils, is added. In some instances, the epoxidized oil can be omitted and the mercapto ester will function as a co-heat stabilizer in addition to functioning as a sterilizing stabilizer.

Most useful Ca and Zn carboxylates are salts of aliphatic acids having 4 to 30 carbon atoms in their molecule. Preferred compounds are Ca and Zn soaps of fatty C$_6$ to C$_{18}$ acids. Thus, for example, in conjunction with epoxy-soya oil, epoxy-linseed oil or a similar epoxidized drying oil, good results are obtained with mixtures of Ca hexanoate, octanoate, decanoate, undecanoate, dodecanoate, tetradecanoate, hexadecanoate, octadecanoate, etc. with a similar but not necessarily identical Zn salt.

In current practice, laurates, pamitates, oleates, myristates, stearates, hydroxy-stearates and linoleates of Ca and Zn are very useful.

Though various proportions of Ca compound, Zn compound, and epoxidized oil may be used, best results are obtained with ponderal ratios Ca salt/Zn salt comprised between 1:3 and 3:1; preferred ratios are in the range of 1:1.5 to 1.5:1.

The best proportion of the total Ca and Zn salt in the resin to be stabilized is about 0.4 to 2% by weight and preferably 0.5 to 1.5.

As to the epoxidized oil, which has to be added when the Ca—Zn compounds are used, its proportion by weight is 2 to 20 times that of the total Ca salt+Zn salt; the preferred range is 4 to 12 times.

The proportion of the metallic stabilizer can be the same as that used in the known technique for the heat stabilization of the material, that is to say in general from 0.01 to 5% by weight of the resin, and more frequently of the order of 0.5 to 2.5%. Morover, one practical method of putting the invention into practice consists of furnishing a resin ready to be used, containing all the beneficial additives, including the stabilizers against heat, kneading it with heat to a semi-pasty state to incorporate into it one or more ester-thiols according to the invention, and then shaping the composition into the desired form, prior to the treatment with the ionizing radiation. Thus, one can use the compositions described in French patent specification No. 1,440,656, notably those in which the tin is in the form of the thioglycolate. Alternatively, one can use the compositions given in French patent publication No. 2,434,835, and U.S. Pat. Nos. 3,063,963; 3,507,827; 3,970,689 and 2,914,506. These compositions undergo a distinct alteration as soon as the dose of radiation exceeds 0.5 megarad, although they will withstand 1 megarad and more when they incorporate at least one of the mercapto-esters according to the invention. This fact is all the more unexpected because many of the known compositions contain thioglycolic acid, free or in combination, which is in fact a mercaptan, HS—$CH_2COOH$. Nevertheless, these compositions do not withstand doses of 1 megarad or more unless they have incorporated in them one of the special mercaptan esters in accordance with the invention. p As already mentioned above, the mercaptan esters, added to the resin according to the invention, contain one —SH function for 3 to 10 carbon atoms. Preferably, the ester molecule carries two —SH groups and it is advantageous if these groups are located at opposite ends of the chain which forms the molecule. As non-limiting examples, there is now listed a number of mercaptan esters derived from carboxylic monoacids, which meet the objection of the invention.

|  | Ratio SH/C |
|---|---|
| Ethyl thiolactate $CH_3CH$—$COOC_2H_5$<br>$\mid$<br>SH | 1/5 |
| Methyl 6-mercapto caproate<br>$HS(CH_2)_5COOCH_3$ | 1/6 |
| 2-Mercapto ethyl caproate<br>$CH_3(CH_2)_4$—$CH_2CH_2SH$ | 1/8 |
| 2-Mercapto ethyl 6-mercapto caproate<br>$HS$—$(CH_2)_5$—$COO$—$CH_2CH_2SH$ | 1/4 |
| 2-Mercapto ethyl 12-mercapto laurate<br>$HS$—$(CH_2)_{11}$—$COO$—$CH_2CH_2SH$ | 1/7 |

It should be noted in connection with this that thioglycolic acid, if freely used in accordance with the aforementioned patent specifications, is not an ester, and its ratio SH/C is 1 to 2. As seen above, it does not protect against ionizing radiation.

According to one embodiment of the invention, which is particularly interesting, the mercaptan ester, incorporated into the resin, is derived from carboxylic diacid or from a polyol and carries two —SH groups, respectively, at opposite ends of the molecule. These preferred mercaptan esters can be represented by the general formula:

$$HS-(CH_2)_n-Z-(CH_2)_m-Z-(CH_2)_n-SH \text{ tm}$$
(1)

where Z represents the carboxy group

in which the carbon atom is linked to a carbon atom of the chain $(CH_2)_n$ or of the chain $(CH_2)_m$. The whole number n can vary from 1 to 9 and m from 1 to 18, but on condition that the sum $(2n+m)$ totals at least 4.

Each of the chains —$(CH_2)_n$ and —$(CH_2)_m$ can in addition carry substituents; —OH or —SH groups are particularly suitable for this.

From what has been stated above, it will be seen that the mercaptan function —SH can be found in the acid residue and/or in the alcohol residue of the ester; in effect, the ester of formula (1) can result from the esterification of (i) a polyol $HO(CH_2)_mOH$ with 2 moles of acid $HS(CH_2)_nCOOH$ or of (ii) a diacid $HOOC(CH_2)_mCOOH$ with 2 moles of a thio-alcohol $HS(CH_2)_nOH$, wherein each of these alcohols and acids can carry other —OH and/or —SH groups.

As non-limiting examples of compounds in accordance with formula (1) according to the invention, there are the following substances:

|  | Ratio SH/C |
|---|---|
| Ethylene glycol bis(mercapto-acetate)<br>$HSCH_2CO$—$CH_2CH_2$—$OCCH_2SH$<br>$\phantom{HSCH_2}\|\|\phantom{CH_2CH_2OCCH_2}\|\|$<br>$\phantom{HSCH_2}O\phantom{CH_2CH_2OCCH_2}O$ | 1/3 |
| Ethylene glycol bis(2-mercapto propionate)<br>$HSCH_2CH_2CO$—$CH_2CH_2$—$OCCH_2CH_2SH$<br>$\phantom{HSCH_2CH_2}\|\|\phantom{CH_2CH_2}\|\|$<br>$\phantom{HSCH_2CH_2}O\phantom{CH_2CH_2}O$ | 1/4 |
| Glyceryl bis(mercapto-acetate)<br>$HSCH_2CO$—$CH_2CHCH_2$—$OCCH_2SH$<br>$\phantom{HSCH_2}\|\|\phantom{CH_2}\|\phantom{CH_2}\|\|$<br>$\phantom{HSCH_2}O\phantom{CH_2}OH\phantom{CH_2}O$ | 1/3.5 |
| Diethylene glycol bis(mercapto-acetate)<br>$HSCH_2CO$—$CH_2CH_2$—$O$—$CH_2CH_2$—$OCCH_2SH$<br>$\phantom{HSCH_2}\|\|\phantom{CH_2CH_2OCH_2CH_2}\|\|$<br>$\phantom{HSCH_2}O\phantom{CH_2CH_2OCH_2CH_2}O$ | 1/4 |
| 2,3-Butanediol bis(3-mercapto-butyrate)<br>$HSCH_2CH_2CH_2CO$—CH—CH—$OCCH_2CH_2CH_2SH$<br>$\phantom{HSCH_2CH_2CH_2}\|\|\phantom{C}\|\phantom{CC}\|\phantom{OC}\|\|$<br>$\phantom{HSCH_2CH_2CH_2}O\phantom{C}CH_3\phantom{}CH_3\phantom{O}O$ | 1/6 |
| Pentaerythrityl bis(2-mercapto propionate) | 1/5.5 |

| -continued | Ratio SH/C |
|---|---|
| HSCH₂CH₂CO—CH₂—C(CH₂OH)(CH₂OH)—CH₂OCCH₂CH₂SH (with =O on both carbonyls) | |
| Pentaerythrityl tris(2-mercapto propionate) | 1/4.66 |
| HSCH₂CH₂CO—CH₂—C(CH₂OH)(CH₂—OCCH₂CH₂SH)—CH₂—OCCH₂CH₂SH | |
| 2,4-Pentanediol 3-thiol bis(7-mercapto caprylate) | 1/7 |
| HS(CH₂)₇CO—CH(CH₃)—CH(SH)—CH(CH₃)—OC(CH₂)₇SH | |
| Di(3-mercapto propyl)malonate | 1/4.5 |
| HSCH₂CH₂CH₂—OC—CH₂—CO—CH₂CH₂CH₂SH | |
| Di(4-mercapto butyl)succinate | 1/6 |
| HSCH₂CH₂CH₂CH₂—OC—CH₂CH₂—CO—CH₂CH₂CH₂CH₂SH | |
| Di(2-mercapto ethyl)hydroxy-succinate | 1/4 |
| HSCH₂CH₂—OC—CHCH₂—CO—CH₂CH₂SH (OH on CH) | |
| Di(6-mercapto hexyl)hydroxy-succinate | 1/8 |
| HS(CH₂)₆—OC—CHCH₂—CO—(CH₂)₆SH (OH on CH) | |
| Di(7-mercapto heptyl)glutarate | 1/9.5 |
| HS(CH₂)₇—OC—CH₂CH₂CH₂—CO—(CH₂)₇SH | |
| Di(2-mercapto ethyl)adipate | 1/5 |
| HSCH₂CH₂—OC—(CH₂)₄—CO—CH₂CH₂SH | |
| Di(2-mercapto ethyl)suberate | 1/6 |
| HSCH₂CH₂—OC—(CH₂)₆—CO—CH₂CH₂SH | |
| Di(3-mercapto propyl)sebacate | 1/8 |
| HSCH₂CH₂CH₂—OC—(CH₂)₈—CO—CH₂CH₂CH₂SH | |

Although the adjunction of the compounds given above enables one to sterilize objects made of polyvinyl chloride with doses of gamma rays exceeding 2 megarads, one can scarcely exceed 0.5 megarads with 2-mercapto ethyl stearate (ratio SH/C=1/20), a compound which, according to French patent publication No. 2,434,835, is an excellent heat stabilizer when it is used jointly with organo-stannic compounds.

The proportions of mercaptan ester, according to the invention, to be added to the polymer, before it is to be subjected to ionizing radiation, are generally of the same order as those of stannic or antimonious stabilizers. Preferably, these range between 0.1 and 6% by weight, depending upon the nature of the polymer and the nature of the mercaptan or mercaptans which are chosen, as well as in dependence upon the doses of radiation to be used. Within these limits, the protective effect increases with increasing percentage of the mercaptan ester. In practice, the recommended proportion is from 0.5 to 5%, especially from 2 to 4%, of the weight of the polymer.

The incorporation of these adjuvants takes place by kneading at a temperature which is high enough to bring about considerable softening of the resin being treated.

Some, but not all, of the metallic heat stabilizers will undergo an equilibrium reaction with the mercapto ester as is known (see, e.g., U.K. Pat. No. 1,117,652). For example the following reactions can occur:

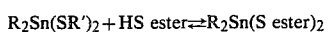

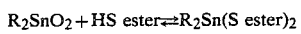

The equilibrium constants of these reactions can vary considerably. In these systems where reaction does occur, the formation of the equilibrium product has not been observed to deleteriously affect the sterilization stabilization. As is apparent from this fact, the desired system can be realized by admixing the equilibrium product (whether or not made by an equilibrium reaction) to the polymer.

The compositions according to the invention can also contain other usual ingredients, such as, for example, agents which facilitate working, reinforcing agents, pigments, lubricants, or even supplementary thermal stabilizers of the polymers of vinyl chloride.

The invention is illustrated by the following non-limiting examples.

EXAMPLES 1 to 6

Irradiation tests with gamma rays emitted by a cobalt 60 source were carried out on a composition of polyvinyl chloride of the type suitable for the molding of hollow bodies, especially containers, and for making transparent or opaque films and sheets. In this composition were incorporated various mercaptan esters, prior to irradiation, in order to see how bottles made of this material would behave when sterilized by gamma rays. The resin was a polyvinyl chloride (PVC) with fluidity index K-57, with the following added ingredients, according to known techniques. For 100 parts by weight of PVC the composition contained:

0.9 parts of working additive, a polyalkyl acrylate sold under the trade name "PARALOID K 120 N" by the company ROEHM & HAAS;

0.7 parts of an anti-caking additive, styrene-alkyl-acrylate copolymer, known under the trade name "PARALOID K 175" from ROEHM & HAAS;

10 parts of shock-resisting strengthener, methacrylate-butadiene-styrene terpolymer, known under the trade name "KANE ACE-B 28 A" (obtainable from the company KANEGAFUCHI of Japan);
1.5 parts of heat stabilizer;
di-n.octyl di(iso-octyl mercapto-acetate)tin

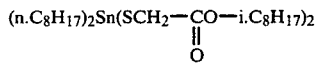

3 parts of heat co-stabilizer, thio-ethylene glycol bis-βaminocrotonate

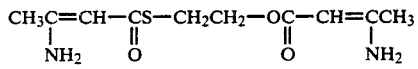

obtainable as a commercial product "Irgastab A 70" from the company CIBA-GEIGY;
1.2 parts of lubricant, glyceryl monostearate.

The composition was mixed in a Papenmeier fast blender until the temperature reached 100° C. From the homogeneous mixture thus obtained, a series of 50×40 mm plates were produced with thicknesses of 4 mm, 2 mm and 1 mm, respectively, by injection, by means of a Negri-Bossi type V7-9 F. AS machine. In other portions of the same composition, mercaptan esters in accordance with the invention were incorporated in the Papenmeier blender, and, for each of these esters, a series of plates with the same thickness dimensions as given above were prepared.

The plates were then subjected to gamma radiation from a cobalt 60 source. For each series, the irradiation was given at doses of 0.46, 0.90 and 2.76 megarads.

All the plates having been practically colorless at the start, the coloration was observed after each irradiation treatment.

The following Table summarizes the results of these observations: the intensity of the coloration (yellowish or reddish) is denoted by the symbols − or +:
 − indicates that the specimen remained practically colorless;
 + indicates a weak coloration;
 ++ indicates an average coloration;
 +++ indicates a strong coloration;
 ++++ indicates a very strong coloration.

TABLE I

| Example No. | Added mercaptan ester and its % to the PVC | | Radiation dosage in megarads | | |
|---|---|---|---|---|---|
| | | | 0.46 | 0.90 | 2.76 |
| | | | | Coloration | |
| 1 | none | | ++ | +++ | ++++ |
| 2 | Glyceryl bis(mercapto acetate) | 3% | − | − | − |
| 3 | Di(2-mercapto ethyl)-hydroxy-succinate | 2% | − | − | ++ |
| 4 | Di(2-mercapto ethyl)-hydroxy-succinate | 3% | − | − | + |
| 5 | Di(2-mercapto ethyl)-adipate | 3% | − | − | ++ |
| 6 | 2-mercapto ethyl stearate | 3% | + | ++ | +++ |

The comparison of Examples 2 to 5 with Examples 1 and 6 shows a considerable improvement in the response to the ionizing radiation, thanks to the incorporation of the special mercaptan esters according to the invention; it shows at the same time that the thio- group, present in the organo-stannic compound and in the amino-crotonate of the treated composition, does not inhibit the adverse effects of the gamma rays, any more than the mercapto group of the stearate does (Example 6). Although the stearate slightly improved the behavior of the resin, it is substantially ineffective except for the dose at 0.46 megarads.

On the contrary, the mercaptan esters according to the invention all permit doses of up to 0.9 megarad, which is generally sufficient. The glyceryl bis(mercapto-acetate) (Example 2) makes it possible to apply the maximum dose of 2.76 megarads, which is quite remarkable. Example 4 shows that with di(2-mercapto-ethyl)-hydroxy-succinate one can go up to a dose very close to 2.76 megarads.

EXAMPLES 7 to 12

The same operational procedure as described above for Examples 1 to 6 was applied to the same polyvinyl chloride into which was incorporated 1.8% by weight of di-n.octyl di(isooctyl mercapto-acetate)tin, as well as heat stabilizer, but without the addition of the anti-caking substance, the shock-absorbing strengthener, or the working additive. In these Examples 8 to 12, the same proportions of the same mercaptans were added as in the respective Examples 2 to 6.

After the gamma ray irradiation, it was found that the same results were obtained for Examples 7 to 12 as were obtained for Examples 1 to 6, respectively.

EXAMPLES 13 to 18

The tests of Examples 7 to 12, but without any adjuvants, other than the stannic compound and the mercaptan, were repeated, but the stannic stabilizer used was dibutyl-tin maleate

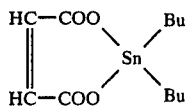

at a proportion of 2% in place of that of the preceding Examples. In Example 13, no other additive at all was added while in Examples 14 to 18, 2.7% of a mercaptan was introduced, the composition of which was as set out in the following Table II of results.

TABLE II

| Example No. | Added mercaptan ester (2.7%) | Radiation dosage in megarads | | |
|---|---|---|---|---|
| | | 0.46 | 0.90 | 2.76 |
| | | | Coloration | |
| 13 | None | ++ | +++ | ++++ |
| 14 | Ethylene glycol bis-(mercapto-acetate) | − | − | + |
| 15 | Di(3-mercapto propyl)-malonate | − | − | − |
| 16 | Di(4-mercapto butyl) succinate | − | − | ++ |
| 17 | Methyl 6-mercapto caproate | − | − | + |
| 18 | Ethyl mercapto-stearate | + | ++ | +++ |

It will be seen that the mercaptan esters Nos. 14 to 17, in which the mole ratio C/SH is between 3 and 10, afford good protection against the effects of the gamma rays. On the other hand, the ethyl mercapto-stearate (C/SH=20), known as excellent heat stabilizer, gives poor results in the presence of gamma rays.

EXAMPLES 19 to 24

In a series of mixtures of polyvinyl chloride with 1.7% of stannic compound and 2.7% of glyceryl bis(-mercapto acetate), without other adjuvants, the nature of the stannic compound was varied. The compositions obtained were subjected to irradiation, as in the preceding Examples.

The tin stabilizers which were tried were:

Example
19—Dilaurate of dibutyl-tin
20—Dimethyl di(myristyl mercapto-acetate)tin
21—Dibutyl di(2-mercapto ethyl stearate)tin
22—Monobutyl tri(ethyl mercapto-oleate)tin
23—Monobutyl mercapto-acetate of isooctyl tin sulfide
24—Compound $BuO(SnBu_2O)_2Bu$ In all these cases, the presence of glyceryl bis-(mercapto-acetate) improved the behavior with respect to the gamma rays to the same degree as in Examples 2 to 5 (Table I above).

EXAMPLE 25

In Example 8, where the added mecaptan ester was glyceryl bis(mercapto-acetate), just as in Example 2, the stannic stabilizer was replaced by the same proportion of n.octyl di(isooctyl mercapto-acetate)antimony.

The colorations after irradiation were similar to those obtained in Example 2.

EXAMPLE 26

Example 25 was repeated, but the antimony heat stabilizer was tri(isooctyl mercapto-acetate)antimony. The improvement in the response to the gamma rays, brought about by the glyceryl bis(mercapto-acetate), was similar to that of Example 2.

EXAMPLE 27

The PVC composition of Example 1 has been used for making 100 ml flasks (A) by usual blowing extrusion. Similar flasks (B) were made after the composition has been added with 3 weight % of glyceryl bis(mercapto-acetate).

The two sorts of flasks were then irradiated in three successive passes with rays.

The color was as follows:

|  | (A) | (B) |
|---|---|---|
| after a 1st pass of a 2.7 Mrad dose: | strongly yellow | substantially no change |
| after a 2nd pass of a 2.6 Mrad dose: | brown | very slightly yellow |
| after a 3rd pass of a 3.0 Mrad dose: | dark brown | yellowish |

Thus, stabilized according to the invention, the flasks showed an excellent resistance to gamma rays even with a total dose of 2.7+2.6=5.3 Mrad;

With 2.7+2.6+3.0=8.3 Mrad, they still preserved a quite clear color.

EXAMPLE 28

In the composition of resin of Examples 1 to 6, the Sn heat stabilizer and the aminocrotonate co-stabilizer were omitted and replaced by 0.29 parts of calcium stearate, 0.32 parts of zinc stearate and 4.5 parts of soya bean epoxidized oil.

The tests described with respect to Table I above were repeated on flasks previously made with the compositions by extrusion on a "Hesta" machine.

Radiation dosages were this time 0.5 MR, 1 MR and 2.5 MR. Substantially the same results were obtained as above in Examples 1–6, except that the initial color of the flasks was slightly bluish.

EXAMPLE 29

The same polyvinyl chloride as in Examples 1–6 has been stabilized by the addition by weight of:
3% epoxidized soya bean oil
0.29% calcium stearate
0.32% zinc Stearate
3% glyceryl bis(mercapto-acetate)

Then tests were carried out in the manner described in Example 27, comparatively with a control sample. Successive irradiations with 2.7 MR, 2.6 MR and 3.0 MR gave substantially the same results as those in Example 27.

We claim:

1. In a process for the ionizing radiation of a vinylic halide polymer at doses sufficient to cause sterilization, the polymer incorporating a composition which is effective for preventing the discoloration produced thereby, the improvement which comprises said composition comprising a metallic heat stabilizer, and a carboxylic acid ester carrying at least one mercaptan function in the proportion of one SH group for each 3 to 10 carbon atoms.

2. A process as claimed in claim 1, in which the metallic heat stabilizer is an organo-tin or organic antimony containing heat stabilizer.

3. A process as claimed in claim 2, in which the heat stabilizer is an organo-stannic compound.

4. A process as claimed in claim 2, in which the heat stabilizer is an organo-antimonious compound.

5. A process as claimed in claim 2, in which the irradiation is carried out at a dosage of 0.5 to 2.8 megarads.

6. A process as claimed in claim 2, in which the mercaptan ester is a dithiol in which the two —SH groups are at opposite ends of the molecular chain.

7. A process as claimed in claim 2, in which the mercaptan ester has the structure $HS(CH_2)_n—Z—(CH_2)_m—Z—(CH_2)_nSH$ where Z represents the carboxy group

where the carbon atom is connected to a carbon atom of the chain $—(CH_2)_n$ or of the chain $—(CH_2)_m$, where n is a whole number from 1 to 9 and m is a whole number from 1 to 18, and the sum (2n+m) is at least 4.

8. A process as claimed in claim 7, in which the mercaptan ester is a diester of 2 moles of a carboxylic mercapto-acid with 1 mole of a polyol.

9. A process as claimed in claim 8, in which the ester is glyceryl 1,3-bis(mercapto-acetate).

10. A process as claimed in claim 7, in which the mercaptan ester is a diester of 1 mole of a carboxylic diacid with 2 moles of a mercaptan having an alcohol group.

11. A process as claimed in claim 9, in which the mercaptan ester is a malonate, succinate, hydroxy-succinate, glutarate, adipate, suberate or sebacate of a di(-mercapto-alkyl), the alkyl being from $C_1$ to $C_9$.

12. A process as claimed in claim 2, in which the polymer is polyvinyl chloride, the amount of the said mercapto-ester incorporated is 0.5% to 6% by weight, and the ionizing radiation is gamma rays.

13. A process as claimed in claim 2, in which the amount of heat stabilizer is 0.01–5 weight percent and the amount of mercapto-ester is 0.1–6 weight percent.

14. A process as claimed in claim 13, in which the amount of heat stabilizer is 0.5–2.5% and the amount of mercapto-ester is 0.5–5%.

15. A process as claimed in claim 14, in which the amount of mercapto-ester is 2–4 weight percent.

16. A process as claimed in claim 2, in which the ester is selected from the group consisting of di(2-mercapto-ethyl)-hydroxysuccinate, di(2-mercaptoethyl)-adipate, ethylene glycol bis(mercapto-acetate), di(3-mercapto-propyl)malonate, di(4-mercaptobutyl)succinate, and methyl-6-mercapto caproate.

17. A process as claimed in claim 1, in which the amount of heat stabilizer is 0.5–2.5% and the amount of mercapto-ester is 0.5–5%.

18. A process as claimed in claim 17, in which the amount of mercapto-ester is 2–4 weight percent.

19. A process as claimed in claim 1, in which the ester is selected from the group consisting of di(2-mercapto-ethyl)-hydroxysuccinate, di(2-mercaptoethyl)-adipate, ethylene glycol bis(mercapto-acetate), di(3-mercapto-propyl)malonate, di(4-mercaptobutyl)succinate, and methyl-6-mercapto caproate.

20. A process according to claim 1, in which the metallic heat stabiizer is of the formula $$R_2Sn\begin{matrix}R'\\R''\end{matrix} \quad R_2Sn\begin{matrix}YR'\\YR''\end{matrix} \quad \text{or} \quad R'''{-}S{-}Sn\begin{matrix}R'\\R''\\R'''\end{matrix}$$

where Y is O or S and R, R', R'' and R''' are $C_{1-18}$ alkyl.

21. A process according to claim 1, in which the metallic heat stabilizer is of the formula $$\begin{matrix}R\\ \phantom{}\\R'\end{matrix}Sn\begin{matrix}R''\\ \phantom{}\\R'''\end{matrix} \quad RSn(YR')_3 \quad RSn\begin{matrix}Y\\ \phantom{}\\OH\end{matrix}$$

$$R{-}Y{-}\left[\begin{matrix}R\\|\\Sn{-}Y\\|\\R\end{matrix}\right]_2{-}R \quad RnSn(SR'COOR'')_{4-n}$$

$$RnSn(OOCR')_{4-n} \text{ or } RnSn(SR'OOCR'')_{4-n}$$

where R, R', R'' and R''' are $C_{1-18}$ alkyl, Y is O or S and n is 1, 2 or 3.

22. A process according to claim 1, in which the metallic heat stabilizer is of the formula $$R_2Sn\begin{matrix}OOC{-}CH\\ \phantom{}\\OOC{-}CH\end{matrix} \quad \text{or} \quad RnSn[OOC(CH_2)_mSH]_{4-n}$$

where R is $C_{1-18}$ alkyl, n is 1, 2 or 3 and m is 1–7.

23. A process according to claim 1, in which said metallic heat stabilizer is of the formula $$RnSb(YR')_{3-n}$$

, $$RnSb[S(CH_2)_tCOOR']_{3-n}$$

where R and R' are $C_{1-18}$ alkyl, n is 0–3, Y is O or S and T is 1–3.

24. A process according to claim 1, wherein said metallic heat stabilizer comprises a calcium carboxylate, a zinc carboxylate and an epoxidized oil.

25. A process according to claim 24, in which said carboxylates have 4 to 30 carbon atoms and the weight of epoxidized oil is 2 to 20 times that of the total weight of the Ca and Zn carboxylates.

26. A process according to claim 25, in which the carboxylates are Ca and Zn soaps of fatty acids having 6 to 18 carbon atoms, the ponderal ratio of Ca soap to the Zn soap is 1:3 to 3:1, the proportion of the total weight of Ca and Zn soap in the resin being 0.4 to 2% while the weight of epoxidized oil is 4 to 12 times that of said total Ca and Zn soaps.

27. A process according to claim 1, in which the organo-tin heat stabilizer is di-n.octyl di(isooctyl mercapto-acetate)tin.

28. In an ionizing radiation sterilized polymer composition comprising a vinylic halide polymer containing a stabilizing composition which is effective for preventing discoloration produced by the sterilization, the improvement which comprises said stabilizing composition comprising a metallic containing heat stabilizer and a carboxylic acid ester carrying at least one mercaptan function in the proportion of one SH group for each 3 to 10 carbon atoms.

29. A sterilized polymer composition as claimed in claim 28, in which the metallic heat stabilizer is an organo-tin or organic antimony containing heat stabilizer.

30. A sterilized polymer composition as claimed in claim 28, in which the polymer is polyvinyl chloride and in which the ester is present in the proportion of 0.5 to 6% by weight of the polymer.

* * * * *